(12) United States Patent
Dhere et al.

(10) Patent No.: US 12,180,527 B2
(45) Date of Patent: Dec. 31, 2024

(54) METHOD FOR REMOVAL OF IMPURITIES FROM BACTERIAL CAPSULAR POLYSACCHARIDE BASED PREPARATIONS

(71) Applicant: Serum Institute of India Private Limited, Pune (IN)

(72) Inventors: Rajeev Mhalasakant Dhere, Pune (IN); Sambhaji Shankar Pisal, Pune (IN); Dattatreya Sarma Annamraju, Pune (IN)

(73) Assignee: Serum Institute of India Private Limited, Pune (IN)

( * ) Notice: Subject to any disclaimer, the term of this patent is extended or adjusted under 35 U.S.C. 154(b) by 0 days.

(21) Appl. No.: 18/212,815

(22) Filed: Jun. 22, 2023

(65) Prior Publication Data
US 2024/0026405 A1    Jan. 25, 2024

Related U.S. Application Data

(62) Division of application No. 16/611,137, filed as application No. PCT/IB2018/053069 on May 3, 2018, now Pat. No. 11,739,356.

(30) Foreign Application Priority Data

May 5, 2017   (IN) .............................. 201721015961

(51) Int. Cl.
  *C12P 19/04*     (2006.01)
  *A61K 39/095*   (2006.01)
  *A61K 39/00*     (2006.01)
(52) U.S. Cl.
  CPC ............ *C12P 19/04* (2013.01); *A61K 39/095* (2013.01); *A61K 2039/6037* (2013.01)
(58) Field of Classification Search
  None
  See application file for complete search history.

(56) References Cited

U.S. PATENT DOCUMENTS 6,891,037 B1    5/2005   Hasler et al.

FOREIGN PATENT DOCUMENTS

| CN | 102653565 A | 9/2012 |
| WO | WO 9832873 A1 | 7/1998 |
| WO | WO 03/007985 A2 | 1/2003 |
| WO | WO 2013/114268 A1 | 8/2013 |
| WO | WO 2014/080423 A2 | 5/2014 |

OTHER PUBLICATIONS

Tapia, M et al., "Meningococcal Serogroup ACWYX Conjugate Vaccine in Malian Toddlers", The New England Journal of Medicine, Jun. 3, 2021; 384:2115-23. DOI: 10.1056/NEJMoa2013615 (nine (9) pages).
Bolgiano, B et al., "Evaluation of Critical Quality Attributes of a Pentavalent (A, C, Y, W, X) Meningococcal Conjugate Vaccine for Global Use", MDPI, Pathogens 2021, 10, 928, https://doi.org/10.3390/pathogens10080928, pp. 1-17 (17 pages).
Chen, W. et al., "Safety and immunogenicity of a pentavalent meningococcal conjugate vaccine containing serogroups A, C, Y, W, and X in healthy adults: a phase 1, single-centre, double-blind, randomized, controlled study", www.Thelancet.com/infection, Published online Aug. 14, 2018, http:/dx.doi.org/10.1016/81473-3099(18)20400-6, pp. 1-9 (nine (9) pages).
Tapia, M. et al., "Meningococcal Serogroup ACWYX Conjugate Vaccine in Malian Toddlers", including Phase II Results, The New England Journal of Medicine, Jun. 3, 2021, vol. 384, No. 22, pp. 2115-2123 (18 pages).
International Search Report, International Application No. PCT/IB2018/053069 (published under WO 2018/203268) (five (5) pages, Sep. 6, 2018).
Written Opinion of the International Searching Authority, International Application No. PCT/IB2018/056039 (published under WO 2018/203269 (eight (8) pages, Nov. 11, 2018).

*Primary Examiner* — Oluwatosin A Ogunbiyi
(74) *Attorney, Agent, or Firm* — Crowell & Moring LLP

(57) ABSTRACT

The present invention relates to an improved process for purification of bacterial capsular polysaccharides, more specifically capsular polysaccharides of gram negative bacteria. The process comprises of concentration and diafiltration of harvest, treatment with anionic detergent and strong alkali followed by centrifugation, diafiltration and cationic detergent based precipitation of bacterial polysaccharides. The process results in significant reduction of endotoxin, protein and nucleic acid impurities thereby providing higher recovery of capsular polysaccharide with the desired O-acetyl levels. Said process is scalable, non-enzymatic, and employs fewer purification steps.

20 Claims, 3 Drawing Sheets

Figure 1: NMR SPECTRA OF Men-C polysaccharide
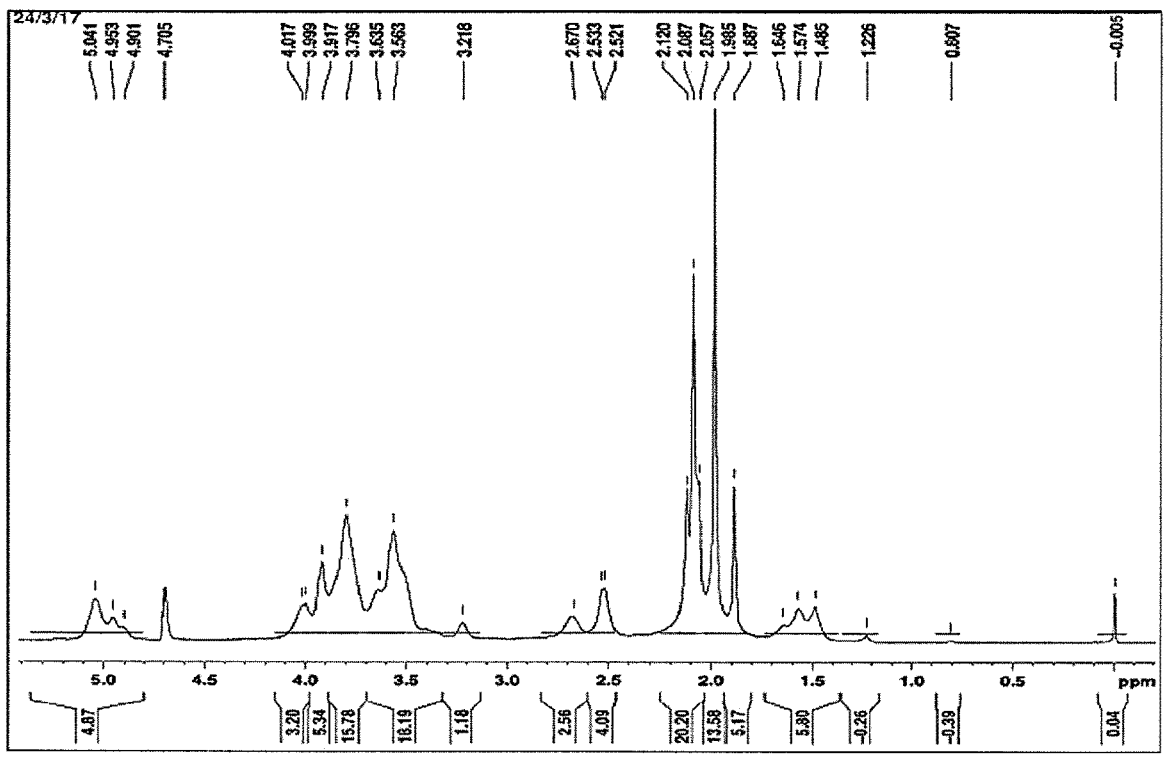
Figure 2: NMR SPECTRA OF Men-Y polysaccharide
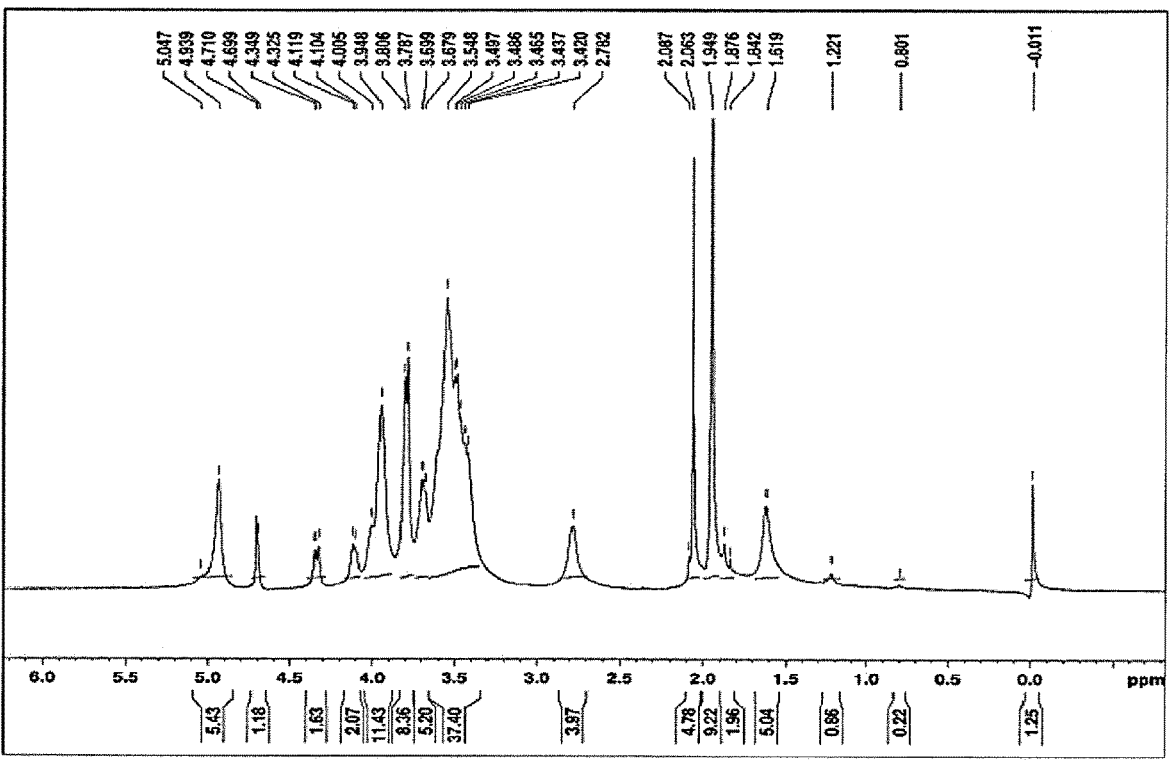

Figure 3: NMR SPECTRA OF Men-W polysaccharide
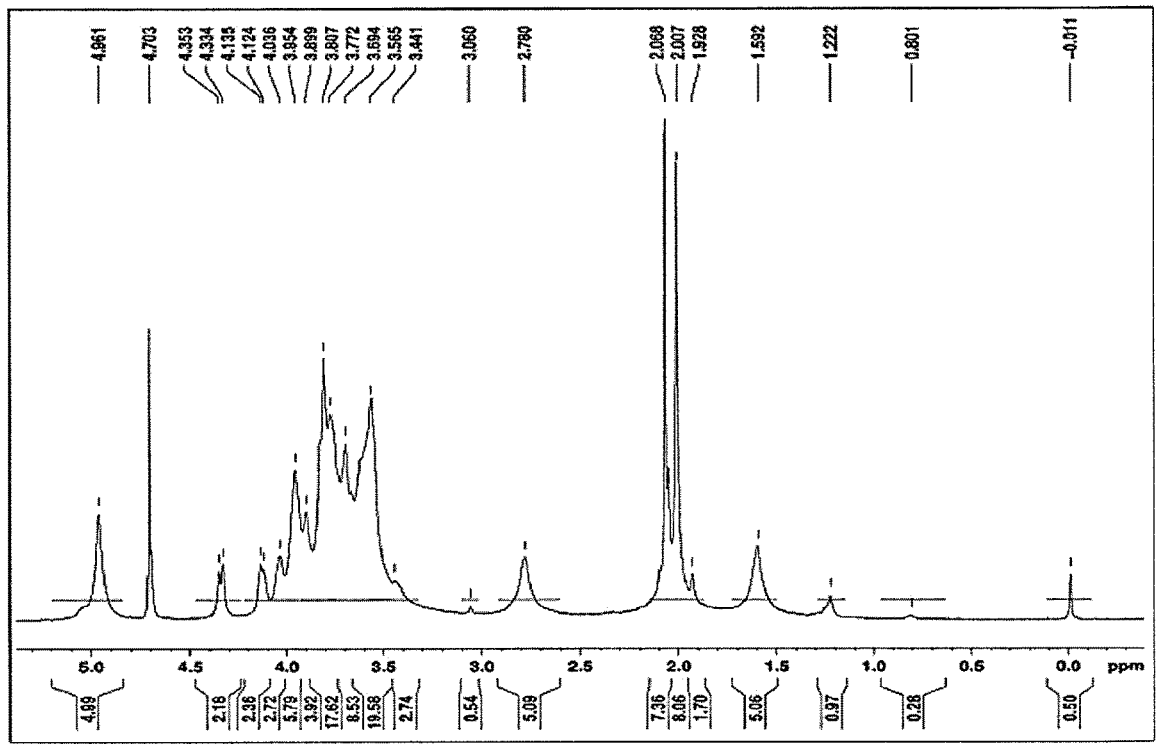
Figure 4  NMR SPECTRA OF Men-A polysaccharide
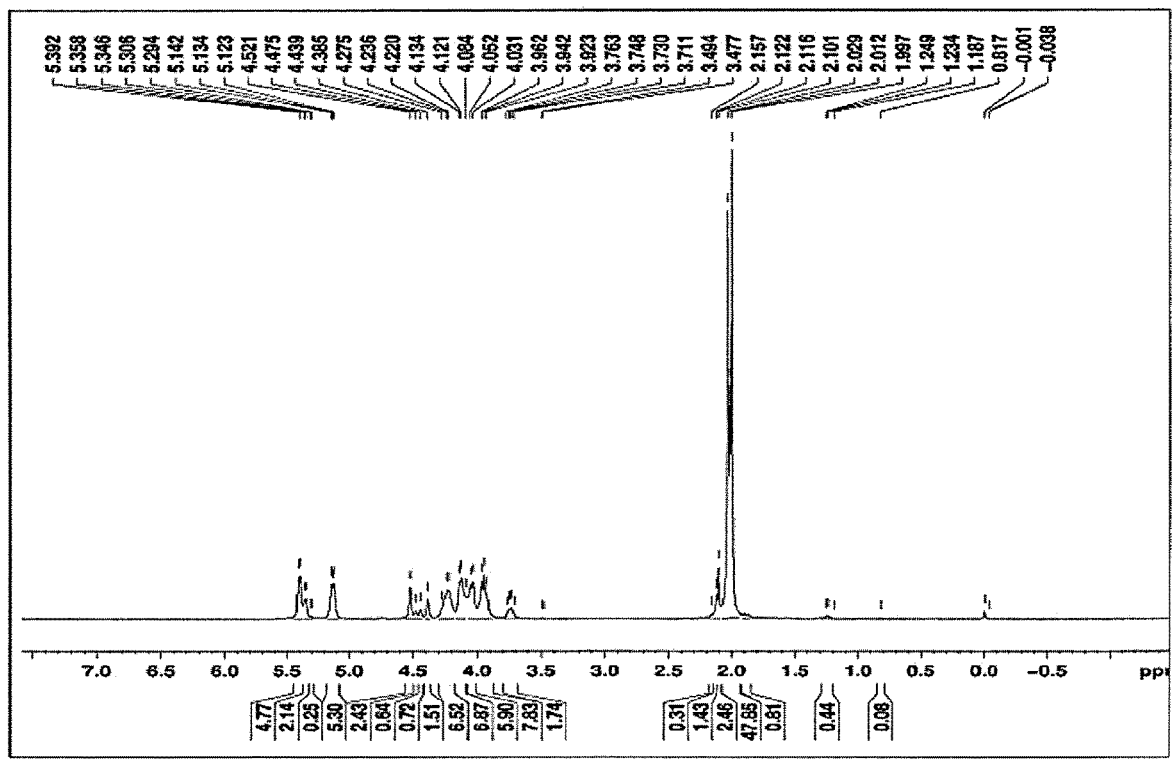

Figure 5: NMR SPECTRA OF Men-X polysaccharide
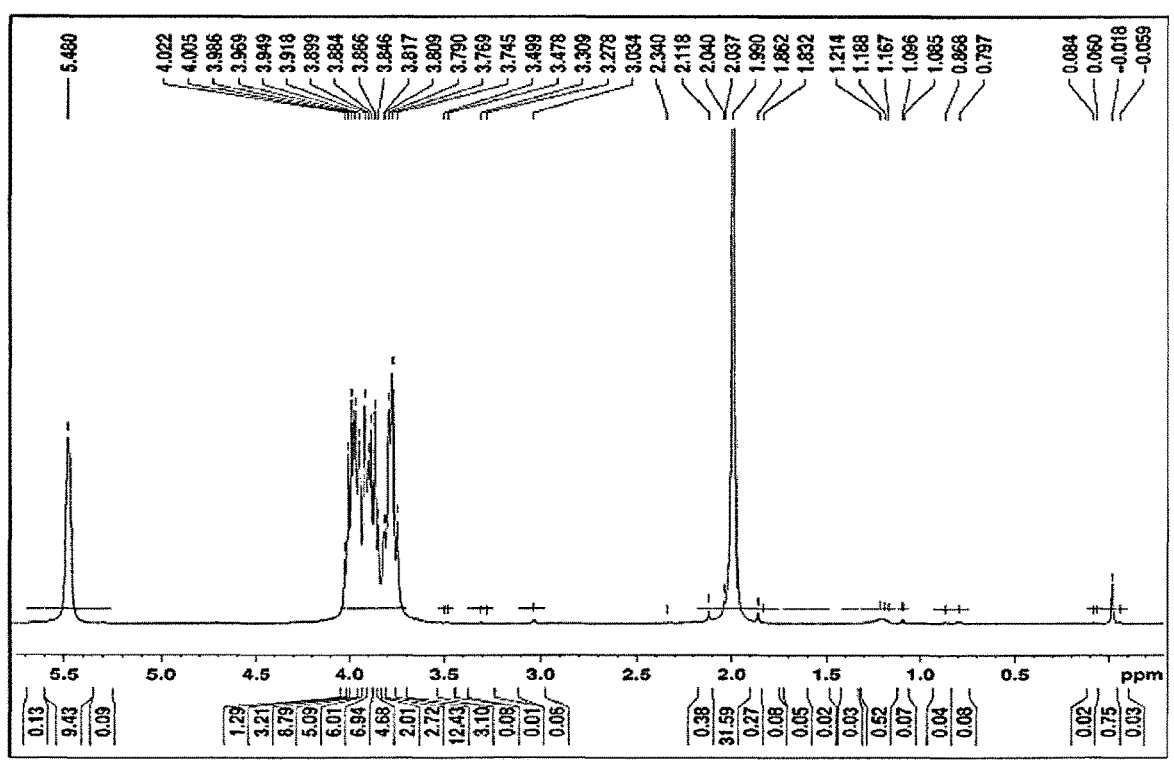

METHOD FOR REMOVAL OF IMPURITIES FROM BACTERIAL CAPSULAR POLYSACCHARIDE BASED PREPARATIONS

CROSS REFERENCE TO RELATED APPLICATIONS

This application is a divisional application of U.S. application Ser. No. 16/611,137, filed Nov. 5, 2019, now U.S. Pat. No. 11,739,356, issued Aug. 29, 2023, which is a 371 U.S. National Stage application of International Application No. PCT/IB2018/053069, filed May 3, 2018, which claims the benefit of and priority to Indian Application No. 201721015961, filed May 5, 2017. The entire contents of each priority application, including their specifications, claims and drawings, are expressly incorporated herein by reference.

FIELD OF THE INVENTION

The invention broadly falls into the field of biotechnology and specifically relates to the harvesting and downstream processing for purification of bacterial capsular polysaccharides.

BACKGROUND OF THE INVENTION

*Neisseria meningitidis* is a major cause of infection of the membranes (meninges) and cerebrospinal fluid (CSF) surrounding the brain and spinal cord, resulting into death and disability worldwide.

*Neisseria meningitidis*, also known as meningococcus, is a gram negative bacterium. According to the structure of polysaccharide capsule, 13 serogroup of *N. meningitidis* have been identified, of which 6 serogroup (A, B, C, W, X and Y) have potential to cause epidemics (Ref: Lee Harrison et al 2011).

Meningitis occurs in small clusters throughout the world with seasonal outbreaks for variable proportions of epidemic bacterial meningitis. The largest burden of meningococcal disease has been observed in the African continent especially sub-Saharan Africa, also known as Meningitis belt. "Centers for Disease Control and Prevention (CDC)" and "World Health Organization" have estimated that meningococcal disease caused 171,000 deaths worldwide in 2000. Also, CDC report confirms the emergence of *Neisseria meningitidis* as a leading cause of meningitis and septicaemia in children and young adults in the United States. Thus, *Neisseria meningitidis* continues to be a public health problem in both developed and developing countries.

In 1996-97, epidemic caused by *Neisseria* Meningitis Serogroup A, more than 250,000 cases of disease and over 25,000 deaths were reported; urging the world health community to pledge for development of vaccine that would eliminate group A meningitis epidemics in Africa.

In 2010, meningococcal A polysaccharide conjugate vaccine i.e. Menafrivac was successfully introduced in the African continent resulting into near disappearance of epidemics caused by *Neisseria meningitidis* serogroup A. With the decreasing influence of *Neisseria meningitidis* serogroup A, influence of other meningococcal serogroup such as Men-C, Men-W, Men-X and Men-Y is on the rise. To counter this dramatic effect, various monovalent and multivalent vaccines comprising above mentioned serogroup have been developed and marketed. Although multivalent A, C, Y and W conjugate vaccines have been licensed since 2005 (Menactra®, Menveo®) for use in children and adults in Canada, the United States of America, and Europe; they are available in the market at very high costs, thus making it unaffordable for rest of the world community.

The serogroup A capsule is composed of repeating units of O-acetylated ($\alpha$1-6)-linked N-acetyl-mannosamine-1-phosphate. Capsular polysaccharides from serogroups B, C, W, and Y are composed of sialic acid derivatives; serogroups B and C express ($\alpha$2→8)- and ($\alpha$2→9)-linked sialic acid homopolymers, and alternating sequences of d-galactose or d-glucose and sialic acid are expressed by serogroups W and Y. The contaminants in the fermentation broth interact differently with repeating moieties present on capsular polysaccharides. Therefore, there is a need for a process that exploits these differences for isolation of different bacterial capsular polysaccharides from different serogroup.

According to WHO Technical Report Series on Meningococcal Conjugate Vaccine, following specification should be met by isolated polysaccharides:

TABLE 1

| Control Parameter | WHO Specification | | |
| --- | --- | --- | --- |
| | Men-C | Men-W | Men-Y |
| Polysaccharide (PS) content | >3 mg/ml | >3 mg/ml | >3 mg/ml |
| Protein impurity | <1% | <5% | <5% |
| Nucleic acid impurity | <1% | <2% | <2% |
| Sialic Acid Content | >80% | >56% | >56% |
| O Acetyl Content | >1.5 mM/gm of PS | >0.3 mM/gm of PS | >0.3 mM/gm of PS |
| Endotoxin content | <100 EU/µg of PS | <100 EU/µg of PS | <100 EU/µg of PS |
| Molecular Size distribution | 75% above 0.5 kD | 80% above 0.5 kD | 80% above 0.5 kD |

The classical purification processes of bacterial capsular PS used in vaccines include several selective precipitations with ethanol and/or cationic detergent, followed by continuous centrifugation, ultra-centrifugation and deproteinization with phenol.

Earliest literature for isolation of *Neisseria meningitidis* polysaccharide from Serogroup A, B and C was published by Gotschlich et al (1969). Gotschlich et al employed cationic detergent Cetavlon (Hexadecyl Lrimethylammonium bromide) to rapidly precipitate the negatively charged polysaccharides from the whole culture, followed by the dissociation of detergent-polysaccharide complex using 0.9 M $CaCl_2$ extraction and centrifugation, ethanol precipitation technique was used for nucleic acid removal whereas the proteins were removed using treatment of polysaccharides with Sodium acetate followed by homogenization with chloroform-containing butanol, an alternative use of hot phenol-water mixture is also reported. Final purification method involved polysaccharide precipitation with ethanol (4-5 times) and acetone. This method involves the inconvenience of using Chloroform and large amount of ethanol. (Ref: T. P. Pato, Master's thesis, Instituto de Quimica, Universidade Federal do Rio de Janeiro, Rio de Janeiro, 2003, p. 95.)

The Tanizaki et al. reported purification process for *Neisseria meningitidis* C polysaccharide wherein the phenol extraction was substituted with proteinase digestion using mixture of proteinase K, nagarse and trypsin; Tangential ultrafiltration in hollow fibre 100 kDa cut-off instead of ultracentrifugation; followed by extensive diafiltration, using a 100 kDa cut-off membrane, performed in 20 mM Tris-HCl buffer containing 0.5% of deoxycholate, to eliminate low molecular weight proteins and lipopolysaccharides (LPS). Despite the use of above modifications, the isolated polysaccharide preparation contained protein and nucleic acid values 2% (w/w) and 1.5% (w/w), respectively. [Ref: Tanizaki et al; Journal of Microbiological Methods Volume 27, Issue 1, September 1996, Pages 19-23 & Goncalves et al 2007; Formatex; Communicating Current Research and Educational Topics and Trends in Applied Microbiology].

T P Pato et al (2006) discloses a modified purification process for Neisseria meningitidis C polysaccharide comprising of a continuous flow centrifugation of the culture for removal of the cells; supernatant concentration by tangential filtration (100 kDa cut-off); addition of 0.5% DOC, heating to 55 OC during 30 min and tangential filtration (100 kDa cutoff); anion exchange chromatography (Source 15Q) and size exclusion chromatography (Sepharose CL-4B). [Ref: T. P. Pato et al./J. Chromatogr. B 832 (2006) 262-267].

U.S. Pat. No. 7,491,517 B2 disclose use of CTAB, Ethanol, Proteinase K, Activated carbon and gel filtration for removal of impurities during purification of Neisseria meningitidis C Polysaccharide. However this multistep process results in polysaccharide recovery loss and activated carbon used may give rise to undesirable leachables.

WO2017006349 disclose use of Zinc acetate/Ammonium sulphate/Sodium citrate for removal of protein contaminants from the N. meningitidis harvested extract. It also discloses use of enzymes like Benzonase, Proteinase K or Nargase for degradation of residual proteins and/or nucleic acid materials, followed by chromatographic purification.

WO2015128798A1 discloses a process for removing impurities from Neisseria meningitidis C polysaccharide. The said process employs incubation at 50-60° C. in presence of anionic detergents like Sodium Deoxycholate or HEPES, deacetylation of crude polysaccharides using 0.5-1.5 M NaOH at 50° C. for 30 minutes to 10 hours, and further purification by diafiltration and Hydrophobic Interaction Chromatography (HTC).

Tian et al discloses a process for purification of Neisseria meningitidis C, W and Y serogroup polysaccharides, comprising of use of CTAB, Ethanol, DOC, Capto Adhere (multimodal anion exchange chromatography), Capto DEAE (Weak anion) and Sephadex G25, wherein endotoxin content is less than 25 EU/mg, Protein content less than 10 mg/g, nucleic acid content between 1-7 mg/g [Ref: Tian et al 2013 GE Healthcare; Application note, 29216880 AA].

The Gotschlich procedure being a multistep process results in substantial loss of product recovery i.e. around 37%. Also use of chemical like phenol can lead to unwanted structural changes in the polysaccharide or protein carrier and also results in undesirable phenolic toxic waste.

U.S. Pat. No. 7,491,517 B2, WO2017006349 and T P Pato et al (2006) procedure makes use of enzymes that help in degradation of proteins and nucleic acid contaminants, however the removal of enzymes and hydrolyzed material is a daunting task and may result into loss of the product of interest. Furthermore, regulatory agencies have restricted the use of animal enzymes in products for humans because of the risk of contamination with prions. The usage of enzymes, besides the fact of high cost, will introduce more regulatory issues in the cGMP framework e.g. the origins of enzymes (from animal or recombinant), enzyme activity variations between different vendors and lots, etc.

WO2017006349 and U.S. Pat. No. 4,686,102 A disclose use of ammonium sulphate for precipitation of protein and nucleic acid contaminants. However, at times it also precipitates capsular polysaccharides, resulting in loss of total polysaccharide.

Sodium Deoxycholate (DOC) is a mild detergent and is one of the most commonly used detergent in polysaccharide purifications. Sodium Deoxycholate with a core steroidal structure is less denaturing and limited in its solubilising strength, it breaks the endotoxins without affecting the chemical structure; and hence upon removal of sodium deoxycholate, endotoxins regain their biological activity. Also, DOC based procedures do not work efficiently for removal of contaminants from polysaccharides, especially Sialic acid containing polysaccharides. This could be due to weak detergent activity of DOC on Lipopolysaccharide-Protein association formed during the downstream processing, resulting in high level of Endotoxins and protein content in the final isolated polysaccharide. Further Sodium deoxycholate being an animal-origin product, even its residual presence in final product may lead to non-acceptance of product by regulatory agencies and certain religious communities.

Chromatographic techniques like Size Exclusion chromatography, Ion exchange chromatography, and hydrophobic interaction chromatography have been successfully used for isolation of bacterial polysaccharides with effective removal of protein and nucleic acid contaminants. Despite the successful isolation of bacterial polysaccharide with WHO specifications, the use of chromatographic techniques involves multistep labour and time consuming sample preparation, involves scalability issues, it drastically compromises the recovery of the capsular polysaccharides and thus is not a feasible low cost option for industrial scale downstream processing.

The downstream processing of biological preparations is root cause for 200-80% of the total production costs (Ansejo and Patrick, 1990), the development of new downstream strategies is essential to reduce the production cost and allow the distribution of the vaccine for the entire population by the public health system.

Currently, method employed to obtain polysaccharides in their purified forms include several steps of detergent treatments and differential precipitation of harvest broth using organic solvent such as ethanol.

However, following two major constrains compel to look for alternative method of purification.

At present, as an initial step of removal of impurities (proteins, nucleic acids and endotoxins) an anionic detergent sodium deoxycholate (DOC) is employed. DOC is an animal origin bile-detergent with a core steroid structure. Due to its bulky structure it has limited solubilizing strength and less denaturing ability on biological macromolecules. In addition, its steady supply with required regulatory certification is limited to a single vendor/supplier.

High consumption of ethanol and inclusion of redundant steps (carbon filtration) makes the process tedious, time consuming and costly.

There remains a significant need of alternative, simple, scalable, cost-effective methods for purifying bacterial polysaccharides for obtaining higher polysaccharide recovery. The present invention provides a robust and affordable downstream purification process for isolation of bacterial capsular polysaccharides, wherein said process results in significant reduction of endotoxin, protein and nucleic acid impurities thereby enabling higher recovery of polysaccharide as well as maintaining desired O-acetyl levels as per WHO specification.

SUMMARY OF INVENTION

The present invention relates to an alternative purification process for bacterial capsular polysaccharides, more specifically capsular polysaccharides of *N. meningitidis*.

The process comprises of concentration and diafiltration of harvest through 100 kD tangential flow filtration, followed by addition of anionic detergent and strong alkali for denaturation of proteins, nucleic acids and lipopolysaccharides. The biological extract is later subjected to centrifugation, diafiltration and CTAB based precipitation of bacterial polysaccharides. The process results in improved polysaccharide recovery, is scalable, non-enzymatic, employs cost effective and less number of purification steps. Said process results in significant reduction of endotoxin, protein and nucleic acid impurities thereby enabling higher recovery of polysaccharide as well as maintaining desired O-acetyl levels.

FIGURES

FIG. 1: NMR spectra OF Men-C polysaccharide
FIG. 2: NMR spectra OF Men-Y polysaccharide
FIG. 3: NMR spectra OF Men-W polysaccharide
FIG. 4: NMR spectra OF Men-A polysaccharide
FIG. 5: NMR spectra OF Men-X polysaccharide

DESCRIPTION

According to a general aspect of the invention, one of the bacterial serogroup of interest was grown in a suitable medium and inactivated using formaldehyde or any commonly known method in the prior art; further subjecting to downstream processing for isolation of purified capsular polysaccharide. The bacteria of interest for isolation of capsular polysaccharide of the instant invention was obtained from a gram negative bacteria selected from genus including but not limited to *Escherichia, Neisseria, Haemophilus, Pseudomonas*, etc.; more preferably capsular polysaccharide expressed by serogroup of *Neisseria meningitidis*. In other aspect of the invention polysaccharide can be derived from group comprising of *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., Group A *Streptococcus*, Group B *Streptococcus* Ia, Ib, II, III, V, VI, or VIII; Group C *Streptococcus, Streptococcus pyogenes, Streptococcus agalactiae, Streptococcus dysgalactiae, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholerae, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi, Leptospira* spp., *Hemophilus ducreyi, Corynebacterium diphtheria, Bordetella pertussis, Bordetella parapertussis, Bordetella bronchiseptica, Hemophilus influenzae, Escherichia coli, Shigella* spp., *Ehrlichia* spp., and *Rickettsia* spp. Polysaccharides of *Streptococcus pneumoniae* type 1, 2, 3, 4, 5, 6A, 6B, 7F, 8, 9A, 9F, 9N, 9V, 10A, 11A, 12F, 14, 15A, 15B, 15C, 17F, 18C, 19F, 19A, 20, 22F, 23B, 23F, 24F, 33F, 35B, 38 and 45; Polysaccharides of *Neisseria meningitidis* serogroup A, B, C, D, W135, X, Y, Z, 29E; and *H. influenzae* type b.

The biological material used during experimentation were as follows:

Polysaccharides were isolated from:

TABLE 2

| Name of the Organism | Strain Designation | Source of Strain |
|---|---|---|
| Neisseria meningitidis A | M1027 | SynCo Biopartners (Netherlands) |
| Neisseria meningitidis C | C11 (60E) | CBER/FDA, USA |
| Neisseria meningitidis W | S877 | CBER/FDA, USA |
| Neisseria meningitidis Y | M10659 | CDC, USA |
| Neisseria meningitidis X | M8210 | CBER/FDA, USA |

Unconjugated carrier protein, i.e. CRM197 or TT. CRM197 was derived from Recombinant Strain CS463-003 (MB101) of *Pseudomonas fluorescens* from Pfenex USA. TT was derived from *Clostridium tetani* (Harvard No 49205) obtained from CRI, National Control Authority, Kasauli, Himachal Pradesh, India. CRI got this strain from NVI, Netherland.

According to a first embodiment of the invention, bacterial capsular polysaccharide was clarified from inactivated harvest using centrifugation; and the supernatant was subjected to diafiltration using 100 kD tangential flow filtration unit. It is very well understood that any other suitable method may be used in place of centrifugation and diafiltration for the concentration of bacterial capsular polysaccharides by a person skilled in the art. In one of the preferred aspect of this embodiment, capsular polysaccharide was derived from *Neisseria Meningitidis* Serogroup A, C, W, Y & X.

According to a second embodiment of the invention, the retentate obtained in first embodiment was subjected to treatment with anionic surfactant/detergent. The anionic detergent is selected from the group comprising of alkyl sulfates, sodium dodecyl sulfate, sodium deoxycholate, sodium dodecyl sulfonate, sodium s-alkyl sulfates, sodium fatty alcohol polyoxyethylene ether sulfates, sodium oleyl sulfate, N-oleoyl poly(amino acid) sodium, sodium alkylbenzene sulfonates, sodium .alpha.-olefin sulfonates, sodium alkyl sulfonates, alpha-sulfo monocarboxylic acid esters, fatty acid sulfoalkyl esters, succinate sulfonate, alkyl naphthalene sulfonates, sodium alkane sulfonates, sodium ligninsulfonate, and sodium alkyl glyceryl ether sulfonates.

Preferably, said anionic surfactant is an alkyl sulphate, more preferably sodium dodecyl sulphate at a final concentration in the range of 0.1% to 4%, more preferably at 1% was added to the retentate and stirred at room temperature for 2 hour. Amphipathic nature of SDS makes it a strong chaotropic agent that not only disrupts the proteins but also solubilises them.

In another aspect of the second embodiment, inactivated harvest can be directly treated with anionic surfactant and further subjected to concentration of capsular polysaccharide resulting in sufficient reduction of impurities thereby making subsequent step of using cationic detergent dispensable.

According to a third embodiment of the invention, strong alkali was added to the mixture obtained from above embodiment and was adjusted to pH between 9-11 with constant stirring at room temperature for 1 hour. The said strong alkali was selected from a group of comprising of Sodium hydroxide, Potassium Hydroxide, Sodium carbonate, Hydroxyl amine, Triethyl amine and Lithium Hydroxide.

According to a preferred aspect of the third embodiment of the invention, said strong alkali i.e. Sodium hydroxide was added at a final concentration between 5-20 M to the mixture obtained from above embodiment and adjusted to pH 10.5 with constant stirring at room temperature for 1 hour.

In another aspect of third embodiment of the invention, alternatively in place of alkali, EDTA and Sodium acetate was added to the mixture obtained from second embodiment, with constant stirring at room temperature for 1 hour.

According to a fourth embodiment of invention, the solution obtained from above embodiment was neutralized (pH 7.0) by addition of a mild organic acid. The said mild organic acid is a combination of one or more acids including formic acid, acetic acid, Propionic acid, Oxalic acid etc. To this neutralized mixture, hydrophilic alcohol, preferably ethanol was added to a final concentration of 30-35% and incubated for couple of hours at room temperature with constant stirring. Hydrophilic alcohol is selected from one of methanol, ethanol, n-propyl alcohol, isopropyl alcohol, acetone, and t-butyl alcohol; or a combination of two or more thereof; and its concentration is <65% or >95%.

According to a fifth embodiment of invention, excess anionic detergent was removed from the solution. The solution obtained from above embodiment was subjected to centrifugation and supernatant was collected. 0.1 M Potassium salt was mixed with the supernatant, and upon its dissolution the mixture was incubated at 2-8° C. for >3 hours. Potassium salt is selected from one of potassium chloride, potassium acetate, potassium sulfate, potassium carbonate, potassium bicarbonate, potassium phosphate, potassium hydrogen phosphate, potassium dihydrogen phosphate, potassium nitrate, and other potassium salts, or a combination of two or more thereof. This step takes advantage of the low solubility of potassium dodecyl sulphate. Upon addition of potassium salt preferably KCl, the SDS in the solution is converted to potassium dodecyl sulphate, being less soluble and is easily precipitated out, resulting in complete removal of SDS. It is very well understood that the concentration of KCl can be varied, to get the desired result by a person skilled in the art. The protocol as mentioned in this embodiment of the invention may be modified as per requirement by the person skilled in the art.

In another aspect of fifth embodiment, excess anionic detergent can be removed from the solution using Gel filtration, Ethanol precipitation, and Ion exchange resins/Amberlite columns.

According to a sixth embodiment of invention, solution obtained from above embodiment was subjected to centrifugation and supernatant was collected. The supernatant was passed through a 0.2μ filter and retentate was diafiltered through 100 kDa tangential flow filtration.

According to a seventh embodiment of invention, retentate obtained from above embodiment was diafiltered using Tris-HCl buffer at a final concentration of 25 mM. It was followed by addition of a cationic detergent to a final concentration of 1-2% and incubated at RT for 1 hour with constant stirring. The cationic detergent(s) is selected from one of cetyltrimethylammonium salt, tetrabutylammonium salt, myristyltrimethylammonium salt and hexadimethrine bromide; or a combination of two or more thereof. It is very well understood that the concentration of cationic detergent may be varied in the range of 0.1% to 4%, to get the desired result by a person skilled in the art. Preferably, cationic detergent is CTAB.

According to an eighth embodiment of invention, solution obtained from above embodiment can be subjected to centrifugation and precipitated CTAB-polysaccharide was collected and dissolved in 30-64% Ethanol. The dissolved mixture can be further subjected to centrifugation for removal of undissolved residues.

According to a ninth embodiment of invention, NaCl was added to a final concentration of 0.1 M to the supernatant obtained from above embodiment under constant stirring. The precipitated polysaccharide was collected and dissolved in 1 M NaCl followed by alcohol precipitation (30-64%).

According to a tenth embodiment of invention, solution obtained from above embodiment was extensively diafiltered by WFI (Water for injection) using 100 kDa tangential flow filtration and passed through 0.2μ filter and stored at or below −20° C. as final bulk.

According to the eleventh embodiment of the invention the purified capsular polysaccharide of *N. meningitidis* Serogroup C, W and Y was obtained as per below procedure:

Serogroup C, W and Y of *N. meningitidis* respectively were grown in a suitable medium and inactivated using formaldehyde;
- Sodium Dodecyl Sulphate was added to this inactivated harvest to a final concentration of 5% and stirred at room temperature for 2 hour;
- Sodium Hydroxide was added to a final concentration of 05-20 mM and adjusted to pH 10.5 with constant stirring at room temperature for 1 hour;
- Solution obtained from above step was neutralized by addition of mild organic acid i.e. acetic acid.
- To this neutralized solution, ethanol was added to a final concentration of 30-35% and incubated for couple of hours with constant stirring.
- Solution obtained from above step was centrifuged and supernatant was collected.
- 0.1 M KCL was added to the supernatant and incubated at 2-8° C. for not less than 3 hour.
- Solution obtained from above step was subjected to centrifugation and supernatant was collected. The supernatant was passed through a 0.2μ filter and retentate was diafiltered using Tris-HCl buffer through 100 kDa MWCO filter tangential flow filtration.
- To retentate obtained from the above step, Tris-HCl buffer was added to a final concentration of 25 mM; further followed by addition of CTAB to a final concentration of 2%; and incubated at RT for not less than 1 hour.
- Solution obtained from above step was centrifuged and precipitate was collected and dissolved in 30-64% Ethanol. The dissolved mixture was further subjected to centrifugation for removal of undissolved residues.
- To supernatant obtained from above step, NaCl was added to a final concentration of 0.1-0.3 M. The precipitated PS is dissolved in 1 M NaCl followed by 30-64% alcohol precipitation.
- Solution obtained from above step was extensively diafiltered against WFI using 100 KDa tangential flow filtration and passed through 0.2μ filter and stored at −20° C. as final bulk.

According to twelfth embodiment of the invention, purification process as mentioned in eleventh embodiment provides

- *N. meningitidis* Serogroup C polysaccharide with a recovery between 60-80%, wherein endotoxin content is less than 50 EU/mg, protein content is less than 0.50% and nucleic acid content less than 0.20%.
- *N. meningitidis* Serogroup Y polysaccharide with a recovery between 60-80%, wherein endotoxin content is less than 50 EU/mg, protein content is less than 0.50% and nucleic acid content less than 0.30%.

N. meningitidis Serogroup W polysaccharide with a recovery between 60-80%, wherein endotoxin content is less than 50 EU/mg, protein content is less than 0.5% and nucleic acid content less than 0.2%.

According to thirteenth embodiment of the invention the purified capsular polysaccharide of *N. meningitidis* Serogroup A & X was obtained as per below procedure:

Serogroup A & X of *N. meningitidis* respectively were grown in a suitable medium and inactivated using formaldehyde;

Sodium Dodecyl Sulphate was added to this inactivated harvest to a final concentration of 1% and stirred at room temperature for 2 hour;

EDTA & Sodium acetate were added to this inactivated harvest to a final concentration of 1% and stirred at room temperature for 2 hour;

ethanol was added to a final concentration of 30-35% and incubated for couple of hours with constant stirring.

Solution obtained from above step was centrifuged and supernatant was collected.

0.1 M KCL was added to the supernatant and incubated at 2-8° C. for >3 hours.

Solution obtained from above step was subjected to centrifugation and supernatant was collected. The supernatant was passed through a 0.2μ filter and retentate was concentrated & diafiltered using 25 mM Tris-HCl through 100 kDa MWCO tangential flow filtration.

CTAB was added to a final concentration of 1-2%; and incubated at RT for not less than 1 hour.

Solution obtained from above step was centrifuged and precipitate was collected and dissolved in 30-64% Ethanol. The dissolved mixture was further subjected to centrifugation for removal of undissolved residues.

To supernatant obtained from above step, NaCl was added to a final concentration of 0.1-0.3 M. The precipitated PS is dissolved in 1 M NaCl followed by 30-64% alcohol precipitation.

Solution obtained from above step was extensively diafiltered against WFI using 100 kDa tangential flow filtration and passed through 0.2μ filter and stored at or below −20'C as final bulk.

According to fourteenth embodiment of the invention, purification process as mentioned in thirteenth embodiment provides

*N. meningitidis* Serogroup A polysaccharide with a recovery between 60-80%, wherein endotoxins content is less than 50 EU/mg, protein content is less than 0.50% and nucleic acid content less than 0.20%.

*N. meningitidis* Serogroup X polysaccharide with a recovery between 60-80%, wherein endotoxins content is less than 50 EU/mg, protein content is less than 0.50% and nucleic acid content less than 0.30%.

According to a fifteenth embodiment of the invention, said purified polysaccharide was conjugated to carrier protein. It is very well understood that the carrier protein used for conjugation with polysaccharides may be any carrier protein known in the art as per requirement by the person skilled in art. The non specific examples of carrier proteins includes carrier protein from a group of but not limited to CRM 197, diphtheria toxoid, tetanus toxoid, pertussis toxoid, *E. coli* LT, *E. coli* ST, exotoxin A from *Pseudomonas aeruginosa*, outer membrane complex c (OMPC), porins, transferrin binding proteins, pneumolysis, pneumococcal surface protein A (PspA), pneumococcal adhesin protein (PsaA), pneumococcal surface proteins BVH-3 and BVH-11, protective antigen (PA) of *Bacillus anthracis*, detoxified edema factor (EF), lethal factor (LF) of *Bacillus anthracis*, ovalbumin, keyhole limpet hemocyanin (KLH), human serum albumin, bovine serum albumin (BSA) and purified protein derivative of tuberculin (PPD).

In other aspect of fifteenth embodiment, before conjugation the polysaccharide purified by the instant method was sized by chemical or mechanical means including but not limited to Sonication, microwave, ozonolysis, ionizing radiation, High pressure cell disruption, homogenizer, Microfluidizer, Sodium acetate, sodium metaperiodate, in-vacuo heating etc.

In another aspect of fifteenth embodiment, the polysaccharide purified by the instant method can be conjugated to a carrier protein using reductive amination, cyanylation, Carbodiimide conjugation chemistry.

According to sixteenth embodiment of the invention, immunogenic composition was prepared. The composition comprised of:

(a) a conjugate of (i) the capsular saccharide of *Neisseria meningitidis* serogroup A and (ii) tetanus toxoid;

(b) a conjugate of (i) capsular saccharide of *Neisseria meningitidis* serogroup C and (ii) CRM197;

(c) a conjugate of (i) capsular saccharide of *Neisseria meningitidis* serogroup Y and (ii) CRM 197;

(d) a conjugate of (i) capsular saccharide of *Neisseria meningitidis* serogroup W135 and (ii) CRM197; and (e) a conjugate of (i) capsular saccharide of *Neisseria meningitidis* serogroup X and (ii) tetanus toxoid.

According to seventeenth embodiment of the invention, endotoxins content can be measured by "Bacterial Endotoxin Test by Kinetic Turbidometric Assay (KTA)" or Rabbit pyrogenicity test; protein content can be measured by Lowry method; and Nucleic acid content can be measured by Spectrophotometry. It is very well understood that any other suitable method may be used for quantification of endotoxin, proteins and nucleic acid content.

In another aspect of seventeenth embodiment, molecular size distribution of purified polysaccharide of *Neisseria meningitidis* serogroup A, C, W, Y & X can be done using size exclusion high performance liquid chromatography.

In another aspect of sixteenth embodiment, O acetyl content can be measured using colorimetric Hestrin assay.

EXAMPLES

Example 1: Production of Bacterial Polysaccharides (Upstream Process of *N. meningitidis* Serogroup C)

Using below mentioned fermentation process, polysaccharides were produced.

Fermentation scale: 300 Liters

Cleaning in place (CIP), Pressure hold test and Sterilization in place (SIP) of fermenter were performed.

After completion of SIP, sterile fermentation medium was aseptically transferred to fermenter.

Composition media

Serogroup C Fermentation Media

TABLE 3

| Ingredient | Quantity (g/L) |
|---|---|
| D-glucose monohydrate | 10 |
| Sodium Chloride | 5.8 |
| L-Arginine | 1 |
| L-Serine | 1 |
| Calcium Chloride | 0.028 |
| Iron (II) Sulfate heptahydrate | 0.01 |
| Ammonium Chloride | 0.3 |

TABLE 3-continued

| Ingredient | Quantity (g/L) |
| --- | --- |
| Di-potassium Hydrogen Phosphate | 4 |
| Yeast Extract | 5 |
| Magnesium Chloride | 0.4 |
| Soya peptone | 3 |
| Casamino Acids | 5 |
| Sodium L-glutamate Monohydrate | 10 |
| Ammonium Sulphate | 1.2 |
| L-Cystine | 0.3 |

Serogroup C Feed Media

TABLE 4

| Ingredient | Quantity (g/L) |
| --- | --- |
| D-glucose monohydrate | 200 |
| Sodium L-glutamate Monohydrate | 150 |
| Casamino Acids | 4 |
| Ammonium chloride | 0.2 |

Dissolved oxygen level was adjusted to desired levels.
Fermentation medium was inoculated with culture organism. Fermenter was operated in fed batch mode for 11 to 14 hrs.
After the culture reaches desired OD at 590 nm, culture in the fermenter was inactivated using formaldehyde.
After completion of incubation, temperature was set to 10±5° C. and followed by cell separation using centrifugation.
Supernatant was collected and subjected to depth filtration; clarified harvest was filtered using 0.2μ filter and transferred for purification.

Results:

TABLE 5

| Parameter | Men-C |
| --- | --- |
| Total PS yield of harvest (mg/L) | 703.33 |
| Endotoxin Impurity (EU/mg of PS) | >500 |
| Protein Impurity (%) | 109 |
| Nucleic Acid Impurity (%) | 12.3 |

Example 2 Production of Capsular Polysaccharides (Upstream Process of *N. meningitidis* Serogroup a, W, X & Y)

Using protocol mentioned in example 1, capsular polysaccharide of *N. meningitidis* Serogroup A, W, X & Y was produced.

Serogroup Y Fermentation Media

TABLE 6

| Ingredient | Quantity (g/L) |
|---|---|
| D-glucose monohydrate | 10 |
| Sodium Chloride | 5.8 |
| Potassium sulfate | 1 |
| L-Arginine | 0.75 |
| L-Serine | 0.75 |
| L-Cysteine | 0.4 |
| Calcium Chloride | 0.025 |
| Iron (II) Sulfate heptahydrate | 0.01 |
| Ammonium Chloride | 0.15 |
| Di-potassium Hydrogen Phosphate | 4 |
| Yeast Extract | 3 |

TABLE 6-continued

| Ingredient | Quantity (g/L) |
|---|---|
| Magnesium Chloride | 0.3 |
| Soya peptone | 3 |
| Casamino Acid | 5 |
| Thiamine hydrochloride | 0.05 |
| Sodium L-glutamate Monohydrate | 10 |
| L-Tryptophan | 0.2 |

Serogroup Y Feed Media

TABLE 7

| Ingredient | Quantity (g/L) |
|---|---|
| D-glucose monohydrate | 200 |
| Sodium L-glutamate Monohydrate | 150 |
| L-Arginine | 1 |
| L-Serine | 1 |
| Soya peptone | 10 |
| Yeast Extract | 16.6 |

Serogroup W Fermentation Media

TABLE 8

| Ingredient | Quantity (g/L) |
|---|---|
| D-glucose monohydrate | 10 |
| Sodium Chloride | 5.8 |
| Potassium sulfate | 1 |
| L-Arginine | 0.75 |
| L-Serine | 0.75 |
| L-Cysteine | 0.4 |
| Calcium Chloride | 0.025 |
| Iron (II) Sulfate heptahydrate | 0.01 |
| Ammonium Chloride | 0.25 |
| Di-potassium Hydrogen Phosphate | 4 |
| Yeast Extract | 3 |
| Magnesium Chloride | 0.3 |
| Soya peptone | 3 |
| Casamino Acid | 5 |
| Thiamine hydrochloride | 0.05 |
| Sodium L-glutamate Monohydrate | 10 |

Serogroup W Feed Media

TABLE 9

| Ingredient | Quantity (g/L) |
|---|---|
| D-glucose monohydrate | 200 |
| Sodium L-glutamate Monohydrate | 150 |
| L-Arginine | 4 |
| L-Serine | 4 |
| Soya peptone | 4 |
| Yeast Extract | 4 |
| Magnesium Chloride | 1.6 |
| Calcium Chloride | 0.2 |
| Ammonium chloride | 0.8 |

Results:

TABLE 10

| Parameter | Men-A | Men-X | Men-W | Men-Y |
|---|---|---|---|---|
| Crude PS (mg/L) | 2540 | 1024 | 733 | 1205 |
| Endotoxin (EU/μg OF PS) | >500 | >500 | >500 | >500 |
| Protein (%) | 19.31 | 18.2 | 60.5 | 38 |
| Nucleic Acid (%) | 1.2 | 1.16 | 12 | 3.3 |

The clarified harvest obtained upon testing, PS (Polysaccharide) content of 1-6 gm/l was observed. This clarified harvest was subjected to further purification.

Example 3: Purification of Capsular Polysaccharides (Downstream Process of *N. meningitidis* Serogroup C) Using SDS Followed by Alcohol Precipitation The crude polysaccharide obtained as per example 1 was mixed with varying concentration of SDS. Ethanol was then added to a final concentration which is about 10% below the concentration at which the polysaccharide begins to precipitate. This was further subjected to filtration.

Concentration of SDS Tested:
  0.1%, 0.5%, 1%, 2%, 3%, 4%, 5%, 6%, 7%, 8%, 9% and 10%

All the above mentioned concentration of SDS showed efficacy regards to impurity reduction. Above 4% SDS, no significant difference was observed in impurity profile.

Optimal impurity reduction especially proteins was observed at 1% SDS.

The purified polysaccharide had endotoxins impurities >100 EU/μg of polysaccharide, whereas the WHO limit is <100 EU/μg of polysaccharide.

Example 4: Purification of Capsular Polysaccharides (Downstream Process of *N. meningitidis* Serogroup C)

Protocol:

Two different set of experiments were carried out, 5 Liter and 300 Liter fermentation scale.

Using below mentioned purification process, polysaccharides were purified.

- Crude polysaccharide obtained as per example 1, was taken in a vessel.
- Crude polysaccharide was 3-6 fold concentrated by TFF using 100 kDa cassette.
- Sodium Dodecyl Sulphate was added to this inactivated harvest to a final concentration of 1% and stirred at room temperature for 2 hour;
- Sodium Hydroxide was added to a final concentration of 08-20 mM and adjusted to pH 10.5 with constant stirring at room temperature for 1 hour;
- Solution obtained from above step was neutralized by addition of Acetic acid.
- To this neutralized solution, ethanol was added to a final concentration of 33% and incubated for couple of hours with constant stirring.
- Solution obtained from above step was centrifuged and supernatant was collected.
- Ethanol concentration was increased to 40%.
- 0.1 M KCL was added to the supernatant and incubated at 2-8° C. for not less than 3 hour.
- Solution obtained from above step was subjected to centrifugation and supernatant was collected. Polysaccharide was precipitated by increasing final concentration of ethanol to 65%.
- Polysaccharide pellet was dissolved in 1 M NaCl. The supernatant was passed through a 0.2μ filter and retentate was diafiltered using 25 mM Tris-HCl buffer through 100 kDa tangential flow filtration, to obtain purified polysaccharide (Stage I).
- Addition of CTAB to a final concentration of 2%; and incubated at RT for 1 hour.
- Solution obtained from above step was centrifuged and precipitate was collected and dissolved in 96% Ethanol. The dissolved mixture was further subjected to centrifugation for removal of undissolved residues.
- To supernatant obtained from above step, NaCl was added to a final concentration of 0.2 M. The precipitated PS is dissolved in 1 M NaCl followed by PS precipitation using 65% alcohol.
- Solution obtained from above step was extensively diafiltered against 0.5 M NaCl, followed by WFI using 100 kD tangential flow filtration and passed through 0.2μ filter and stored at −20° C. as final bulk.

Results:

TABLE 11

| N. Meningitidis | Crude Harvest Polysaccharide | | purified Polysaccharide Stage I | | Purified Polysaccharide Stage II | |
|---|---|---|---|---|---|---|
| | | | Fermentation Scale | | | |
| Serogroup C | 5 L | 300 L | 5 L | 300 L | 5 L | 300 L |
| PS Volume | 1 | 50 | 0.65 | 30 | 0.6 | 18 |
| PS concentration (mg/mL) | 3.87 | 4.22 | 3.83 | 5.62 | 3.08 | 7.33 |
| Total PS (grams) | 3.87 | 211 | 2.48 | 168 | 1.84 | 131.94 |
| Protein Impurity (%) | 93.79 | 109.47 | 0.6 | 0.52 | 0.25 | 0.13 |
| Nucleic acid Impurity (%) | 7.49 | 12.32 | 0.02 | 0.3 | 0.02 | 0.08 |
| Endotoxin Impurity (EU/μg of PS) | NA | NA | <20 | <30 | <20 | 40 |
| Step Recovery (%) | NA | NA | 64.3 | 79.9 | 74.23 | 78.25 |
| Molecular Size by HPLC (kDa) | NA | NA | 434 | 450 | 392 | 376 |
| O-Acetyl content Limit: >1.5 mMol/gm | NA | NA | 2.8 | 2.85 | 2.64 | 2.6 |
| Overall Final Recovery (%) | NA | NA | 64.3 | 79.9 | 64 | 62.5 |

Note:
NA = Not applicable

Two different set of experiments were carried out, 5 Litre and 300 Litre fermentation scale.

It was observed that combined use of anionic detergent and alkali had profound effect on reduction of impurity profile. The impurity level at purification stage I & stage II are well below the WHO specification limits for Men-C polysaccharide.

At 5 liters and 300 liters scale, Protein Impurity (%)=<1%; Nucleic acid Impurity (%)=<0.3%; Endotoxin Impurity (EU/μg of PS)=<40 EU/μg of PS.

At both scales and at purification stage I & stage II, recovery of purified polysaccharide was above 60% on comparison with crude sample.

Example 5: Purification of Capsular Polysaccharides (Downstream Process of *N. meningitidis* Serogroup W & Y)

Protocol:

Two different set of experiments were carried out, 5 L and 300 L fermentation scale.

Using below mentioned purification process, polysaccharides were purified.

Crude polysaccharide obtained as per example 2, was taken in a vessel.

Crude polysaccharide was 3-6 fold concentrated by TFF using 100 kDa cassette.

Sodium Dodecyl Sulphate was added to this inactivated harvest to a final concentration of 1% and stirred at room temperature for 2 hour;

Sodium Hydroxide was added to a final concentration of 08-20 mM and adjusted to pH 10.5 with constant stirring at room temperature for 1 hour;

Solution obtained from above step was neutralized by addition of Acetic acid.

To this neutralized solution, ethanol was added to a final concentration of 33% and incubated for couple of hours with constant stirring.

Solution obtained from above step was centrifuged and supernatant was collected.

0.1 M KCL was added to the supernatant and incubated at 2-8° C. for ~8 hours.

Solution obtained from above step was subjected to centrifugation and supernatant was collected.

The supernatant was passed through a 0.2μ filter and retentate was diafiltered using 25 mM Tris-HCl buffer through 100 kDa tangential flow filtration, to obtain purified polysaccharide (Stage I).

Addition of CTAS to a final concentration of 2%; and incubated at RT for 1 hour.

Solution obtained from above step was centrifuged and precipitate was collected and dissolved in 96% Ethanol. The dissolved mixture was further subjected to centrifugation for removal of undissolved residues.

To supernatant obtained from above step, NaCl was added to a final concentration of 0.25 M. The precipitated PS is dissolved in 1 M NaCl followed by PS precipitation using 65% alcohol.

Solution obtained from above step was extensively diafiltered against WFI using 100 kDa tangential flow filtration and passed through 0.2μ filter and stored at −20° C. as final bulk (Stage II).

Result:

TABLE 12

| N. Meningitidis | Crude Harvest Polysaccharide | | purified Polysaccharide Stage I | | Purified Polysaccharide Stage II | |
| --- | --- | --- | --- | --- | --- | --- |
| | Fermentation Scale | | | | | |
| Serogroup Y | 5 L | 300 L | 5 L | 300 L | 5 L | 300 L |
| PS Volume | 1.25 | 50 | 0.75 | 35 | 0.8 | 29.5 |
| PS concentration (mg/mL) | 5.67 | 7.23 | 7.23 | 7.88 | 5.39 | 8.41 |
| Total PS (grams) | 7.08 | 361.5 | 5.42 | 275.8 | 4.31 | 248 |
| Protein Impurity (%) | 38.62 | 38.03 | 2.21 | 1.64 | 0.16 | 0.08 |
| Nucleic acid Impurity (%) | 1.94 | 3.31 | 0.69 | 0.25 | 0.11 | 0.71 |
| Endotoxin Impurity (EU/μg of PS) | NA | NA | 50 | 56 | 44 | 45 |
| Step Recovery (%) | NA | NA | 76.50 | 76.29 | 79.52 | 89.95 |
| Molecular Size by HPLC (kDa) | NA | NA | 660 | 620 | 608 | 543 |
| O-Acetyl content Limit: >0.3 mMol/gm | NA | NA | 0.85 | 0.8 | 0.79 | 0.75 |
| Overall Final Recovery (%) | NA | NA | 76.50 | 76.29 | 60.83 | 68.62 |

TABLE 13

| N. Meningitidis | Crude Harvest Polysaccharide | | purified Polysaccharide Stage I | | Purified Polysaccharide Stage II | |
| --- | --- | --- | --- | --- | --- | --- |
| | Fermentation Scale | | | | | |
| Serogroup W | 5 L | 300 L | 5 L | 300 L | 5 L | 300 L |
| PS Volume | 1 | 39 | 0.8 | 28.5 | 0.8 | 16.5 |
| PS concentration (mg/mL) | 4.26 | 5.65 | 3.5 | 6.01 | 3.25 | 8.75 |
| Total PS (Grams) | 4.26 | 220 | 2.8 | 171 | 2.6 | 144 |
| Protein Impurity (%) | 62.1 | 60.53 | 3.4 | 2.16 | <0.21 | <0.21 |
| Nucleic acid Impurity (%) | 7.98 | 12 | 0.85 | 1.16 | 0.1 | 0.09 |
| Endotoxin Impurity (EU/μg of PS) | NA | NA | <30 | <40 | <20 | <10 |
| Step Recovery (%) | NA | NA | 65 | 77 | 92 | 84.2 |
| Molecular Size by HPLC (kDa) | NA | NA | 400 | 420 | 395 | 380 |
| O-Acetyl content Limit: >0.3 mMol/gm | NA | NA | 1.21 | 1.15 | 1.05 | 0.99 |
| Overall Final Recovery (%) | NA | NA | 65 | 77 | 61 | 65.4 |

Two different set of experiments were carried out, 5 L and 300 L fermentation scale.

On comparison, it was observed that the impurity level at purification stage I & stage II are well below the WHO specification limits for Men-Y & Men-W polysaccharide.

It was observed that combined use of anionic detergent and alkali had profound effect on reduction of impurity profile. The impurity level at purification stage I & stage II are well below the WHO specification limits for Men-C polysaccharide.

At 5 L and 300 L scale, Protein Impurity (%)=<3.5%; Nucleic acid Impurity (%)=<1.5%; Endotoxin Impurity (EU/μg of PS)=<60 EU/μg of PS.

At both scales and at purification stage I & stage II, recovery of purified polysaccharide was above 60% on comparison with crude sample.

Example 6: Purification of Capsular Polysaccharides (Downstream Process of *N. meningitidis* Serogroup a & X)

Protocol:

Two different set of experiments were carried out, 5 L and 300 L fermentation scale.

Using below mentioned purification process, polysaccharides were purified.

- Crude polysaccharide obtained as per example 2, was taken in a vessel.
- Crude polysaccharide was 3-6 fold concentrated by TFF using 100 kDa cassettes.
- Sodium Dodecyl Sulphate was added to this inactivated harvest to a final concentration of 1% and stirred at room temperature for 2 hour;
- Sodium Acetate, EDTA & Sodium Dodecyl Sulphate was added to a final concentration of 6%, 2 mM & 1% respectively; with constant stirring at room temperature for 1 hour;
- Solution obtained from above step was centrifuged and supernatant was collected.
- 0.1 M KCL was added to the supernatant and incubated at 2-8° C. for ~3 hours.
- Solution obtained from above step was subjected to centrifugation and supernatant was collected.
- The supernatant was passed through a 0.2μ filter and retentate was diafiltered using 25 mM Tris-HCl buffer through 100 kDa tangential flow filtration, to obtain purified polysaccharide (stage I).
- Addition of CTAB to a final concentration of 2%; and incubated at RT for 1 hour.
- Solution obtained from above step was centrifuged and precipitate was collected and dissolved in 96% Ethanol. The dissolved mixture was further subjected to centrifugation for removal of undissolved residues.
- To supernatant obtained from above step, NaCl was added to a final concentration of 0.2 M. The precipitated PS is dissolved in 1 M NaCl followed by 65% alcohol precipitation.
- Solution obtained from above step was extensively diafiltered against WFI using 100 kD tangential flow filtration and passed through 0.2μ filter and stored at −20° C. as final bulk (stage II).

Results:

TABLE 14

| N. Meningitidis Serogroup A | Crude Harvest PS | purified Polysaccharide Stage I | Purified Polysaccharide Stage II |
|---|---|---|---|
| Fermentation Scale | 300L | 300L | 300L |
| PS Volume | 50 | 45 | 30 |
| PS concentration (mg/mL) | 11.44 | 6.63 | 9.75 |
| Total PS (grams) | 572 | 298.35 | 292.5 |
| Protein Impurity (%) | 19.31 | 2.05 | 0.14 |
| Nucleic acid Impurity (%) | 1.22 | 0.12 | 0.05 |
| Endotoxin Impurity (EU/μg of PS) | NA | 29.08 | 35 |
| Residual SDS (ppm) | NA | <5 | <5 |
| Step Recovery (%) | NA | 52 | 98 |
| Molecular Size by HPLC (kDa) | NA | 350 | 306 |
| O-Acetyl content Limit: >2 mMol/gm | NA | 2.69 | 2.65 |
| Overall Final Recovery (%) | NA | 52 | 51 |

TABLE 15

| N. Meningitidis Serogroup X | Crude Harvest PS | purified Polysaccharide Stage I | Purified Polysaccharide Stage II |
|---|---|---|---|
| Fermentation Scale | 300L | 300L | 300L |
| PS Volume | 55 | 40 | 30 |
| PS concentration (mg/mL) | 5.05 | 5.23 | 6.21 |
| Total PS (grams) | 277.75 | 209.2 | 186.30 |
| Protein Impurity (%) | 18.21 | 0.6 | 0.54 |
| Nucleic acid Impurity (%) | 1.16 | 0.76 | 0.14 |
| Endotoxin Impurity (EU/μg of PS) | NA | 30 | 13.79 |
| Residual SDS (ppm) | NA | <5 | <5 |
| Step Recovery (%) | NA | 75.3 | 88.9 |
| Molecular Size by HPLC (kDa) | NA | 485 | 479 |
| Overall Final Recovery (%) | NA | 75.3 | 67.25 |

On comparison, it was observed that the impurity level at purification stage I & stage II are well below the WHO specification limits for Men-A & Men-X polysaccharide.

It was observed that use of anionic detergent had profound effect on reduction of impurity profile. The impurity level at purification stage I & stage II are well below the WHO specification limits for Men-A & Men-X polysaccharide.

At 300 L scale, Protein Impurity (%)=<2.5%; Nucleic acid Impurity (%)=<1%; Endotoxin Impurity (EU/μg of PS)=<40 EU/μg of PS.

At both scales and at purification stage I & stage II, recovery of purified polysaccharide of serogroup X was above 60% and purified polysaccharide of serogroup A was above 50%, on comparison with crude sample.

Example 7: Structural Integrity of the Isolated Polysaccharides (PS)

Refer FIGS. 1-5 for NMR spectra.

Structural integrity of the isolated polysaccharides of *N. meningitidis* serogroup A, C, W, Y & X was verified using Nuclear Magnetic Resonance (NMR.

NMR spectra recorded were comparable and confirmed their identity as partially O-acetylated Meningococcal polysaccharide of serogroup A, C, W, & Y; and N-acetylated polysaccharide of serogroup X.

Example 8

Comparative analysis of Sodium Deoxycholate (DOC) based purification process and the claimed process for purification of polysaccharides.

Sodium Deoxycholate (DOC) based process "An improved method for meningococcus polysaccharide purification Tanizaki et al (Conjugate and Polysaccharide Vaccines, Poster 79, http://neisseria.org/ipnc/1996/Neis1996-chap4.pdf)" was optimized as follows:

100 kD Harvest; DOC+EDTA+NaCAc+ethanol (40%) treatment; Centrifugation, collection of supernatant and 0.2μ filtration; Concentration and Diafiltration; CTAB (3%) treatment at RT; Centrifugation and collection of CTAB-PS pellet; Dissolution of CTAB-PS pellet in 96% ethanol and precipitation by 0.1 M NaCl;

Dissolution of precipitate in 40% ethanol and addition of 1 M NaCl (2-8° C.); Centrifugation and collection of supernatant; Carbon filtration; Precipitation of PS by increasing ethanol concentration; PS pellet dissolution in WFI and concentration and diafiltration with WFI and storage at −20° C. after 0.2μ filtration.

The DOC based process is being widely used across industry for purification of polysaccharides to be used as vaccine antigen.

The impurity profile of polysaccharide obtained by DOC based method was compared with the claimed inventive process.

Results:

TABLE 16

| | | % Final Recovery | % protein | % Nucleic acid | Endotoxin (EU/μg of PS) |
|---|---|---|---|---|---|
| Men-A | DOC | 65 | <0.3 | <0.2 | <20 |
| | SDS | 64 | <0.3 | <0.2 | <20 |
| Men-C | DOC | 65 | <0.3 | <0.2 | <20 |
| | SDS | 62.00 | <0.3 | <0.2 | <20 |
| Men-W | DOC | 60 | <0.5 | <0.5 | <30 |
| | SDS | 70 | <0.5 | <0.5 | <30 |
| Men-Y | DOC | 60 | <0.5 | <0.5 | <30 |
| | SDS | 70 | <0.5 | <0.5 | <30 |
| Men-X | DOC | 65 | <0.3 | <0.2 | <20 |
| | SDS | 70 | <0.3 | <0.2 | <20 |

SDS based inventive method and the DOC based method showed similar results for serogroup A & C, whereas for serogroup W, Y & X SDS method showed improved final recovery as compared to DOC method.

As can be seen by the above results the modified SDS process has clear advantages in terms of both, ease of operation as well as several other advantage such as, DOC being an animal origin component and is non HALAL compliant. DOC is manufactured & supplied by a single vendor throughout the world, whereas SDS is a synthetic detergent, HALAL certified and with several suppliers available globally. DOC breaks down the endotoxins without effecting the chemical composition and once the detergent is removed it can regain its biological activity, whereas SDS owing to its amphipathic nature and higher aggregation number denatures and solubilizes the proteins well and also disrupts endotoxins irreversibly to its monomeric units.

By using SDS a decreased consumption of chemicals and consumables (ethanol, ultra-filters, carbon filters etc) has a distinct advantage. Additionally, use of SDS as a replacement was non-invasive on structural integrity of the polysaccharides.

Example 9

Immunogenic composition as shown below was prepared and tested for immunogenicity.

The composition comprised of:
(a) a conjugate of (i) the capsular saccharide of *Neisseria meningitidis* serogroup A and (ii) tetanus toxoid;
(b) a conjugate of (i) capsular saccharide of *Neisseria meningitidis* serogroup C and (ii) CRM197;
(c) a conjugate of (i) capsular saccharide of *Neisseria meningitidis* serogroup Y and (ii) CRM 197;
(d) a conjugate of (i) capsular saccharide of *Neisseria meningitidis* serogroup W135 and (ii) CRM197; and
(e) a conjugate of (i) capsular saccharide of *Neisseria meningitidis* serogroup X and (ii) tetanus toxoid.

Results:

The immunogenic composition was found to be immunogenic.

ADVANTAGES OF THE INVENTION

The process results in significant reduction of endotoxin, protein and nucleic acid impurities thereby providing higher recovery of capsular polysaccharide with the desired O-acetyl levels. As can be seen by the above results the claimed process has clear advantages in terms of ease of operation, as well as several other advantage such as, Regulatory issue: DOC is an animal origin component and is non HALAL compliant. It is manufactured & supplied by a single vendor throughout the world, whereas SDS is a synthetic detergent, HALAL certified and with several suppliers available globally.

Functional issue: DOC breaks down the endotoxins without effecting the chemical composition and once the detergent is removed it can regains its biological activity, whereas SDS owing to its amphipathic nature and higher aggregation number denatures and solubilizes the proteins well and also disrupts endotoxins irreversibly to its monomeric units By using SDS a decreased consumption of chemicals and consumables (ethanol, ultra-filters, carbon filters etc) was a distinct advantage.

Inventive process of the present patent application results in significant decrease of other cellular impurities. Further, the process provides effective removal of reagents used during the upstream and downstream processing.

Additionally, Inventive process of the present patent application was non-invasive on structural integrity of the polysaccharides, thereby maintaining its immunogenicity.

In view of the many possible embodiments to which the principles of the disclosed invention may be applied, it should be recognized that the illustrated embodiments are only preferred examples of the invention and should not be taken as limiting the scope of the invention.

The invention claimed is:

1. A method for isolation of polysaccharide from *Neisseria meningitidis* selected from serotype C, serotype W, and serotype Y, said method comprising the following steps:
   a) adding an anionic detergent to a crude polysaccharide solution comprising *Neisseria meningitidis* selected from serotype C, serotype W, and serotype Y;
   b) adding alkali to the solution;
   c) neutralizing the pH of the solution;
   d) subjecting the solution to alcohol-based precipitation, followed by centrifugation and retention of supernatant;
   e) removing the anionic detergent present in the supernatant;
   f) concentrating and diafiltrating the polysaccharide;
   wherein the obtained purified polysaccharide from *Neisseria meningitidis* selected from serotype C, serotype W, and serotype Y has a recovery of 60-80%.

2. The method of claim 1, wherein the method further comprises the following steps:
   g) mixing the polysaccharide solution with a cationic detergent;
   h) subjecting the solution of polysaccharide with cationic detergent to centrifugation and collection of a pellet; and
   i) dissolving the pellet in alcohol, followed by a salt-based precipitation of polysaccharide,
   wherein the cationic detergent is selected from the group consisting of cetyltrimethylammonium salt, tetrabutylammonium salt, myristyltrimethylammonium salt, hexadimethrine bromide, and combinations thereof, and wherein the salt used for precipitation is selected from the group consisting of sodium chloride, ammonium chloride, potassium chloride, and combinations thereof.

3. The method of claim 1, wherein the anionic detergent is selected from the group consisting of alkyl sulfates, sodium dodecyl sulfate, sodium deoxycholate, sodium dodecyl sulfonate, sodium s-alkyl sulfates, sodium fatty alcohol polyoxyethylene ether sulfates, sodium oleyl sulfate, N-oleoyl poly (amino acid) sodium, sodium alkylbenzene sulfonates, sodium $\alpha$-olefin sulfonates, sodium alkyl sulfonates, $\alpha$-sulfo monocarboxylic acid esters, fatty acid sulfoalkyl esters, succinate sulfonate, alkyl naphthalene sulfonates, sodium alkane sulfonates, sodium lignin-sulfonate, and sodium alkyl glyceryl ether sulfonates.

4. The method of claim 3, wherein the anionic detergent is sodium dodecyl sulfate, and the concentration of anionic detergent in solution is between 0.1% and 4%.

5. The method of claim 4, wherein the concentration of sodium dodecyl sulfate in solution is in the range of 0.1 to less than 1%.

6. The method of claim 1, wherein the alkali is selected from the group consisting of sodium hydroxide, potassium hydroxide, sodium carbonate, hydroxyl amine, triethylamine, and lithium hydroxide.

7. The method of claim 1, wherein the alkali is sodium hydroxide and the concentration of alkali in solution is between 5 mM and 50 mM, and wherein the pH of the solution after alkali addition is in the range of pH 9-11.

8. The method of claim 7, wherein the concentration of sodium hydroxide in solution is in the range of 5-20 mM.

9. The method of claim 1, wherein the solution is neutralized by addition of an organic acid selected from the group consisting of formic acid, acetic acid, propionic acid, and oxalic acid.

10. The method of claim 1, wherein the removal of the anionic detergent is carried out using at least one or more of potassium salt treatment, gel filtration, ethanol treatment, ion exchange resins, and Amberlite columns.

11. The method of claim 10, wherein the removal of the anionic detergent is carried out using a potassium salt treatment, wherein the potassium salt is selected from the group consisting of potassium chloride, potassium acetate, potassium sulfate, potassium carbonate, potassium bicarbonate, potassium phosphate, potassium hydrogen phosphate, potassium dihydrogen phosphate, potassium nitrate, and combinations thereof.

12. The method of claim 11, wherein the potassium salt is potassium chloride, and wherein the concentration of the potassium salt in the solution is less than 300 mM.

13. The method of claim 12, wherein the concentration of the potassium salt in the solution is 100 mM.

14. The method of claim 2, wherein the cationic detergent is cetyltrimethylammonium bromide, and wherein the concentration of the cationic detergent in the solution is between 0.1% and 3%.

15. The method of claim 14, wherein the concentration of cationic detergent is 1%.

16. The method of claim 1, wherein the alcohol is a hydrophilic alcohol selected from the group consisting of methanol, ethanol, n-propyl alcohol, isopropyl alcohol, acetone, t-butyl alcohol, and combinations thereof.

17. The method of claim 1, wherein the concentration and diafiltration of polysaccharide is done using tangential flow filtration, with a 100 kDa MWCO membrane.

18. The method of claim 2, wherein the salt used for precipitation is sodium chloride, and the concentration of the salt in the solution is between 0.25 M to 2 M.

19. The method of claim 1, wherein (i) purified polysaccharide from *Neisseria meningitidis* serotype C has O-acetylation levels >1.5 mMol/gm, protein impurity <1%, nucleic acid impurity <1%, and endotoxin impurity <50 EU/μg;

(ii) purified polysaccharide from *Neisseria meningitidis* serotype Y has O-acetylation levels >0.3 mMol/gm, protein impurity <5%, nucleic acid impurity <2%, and endotoxin impurity <60 EU/μg; and (iii) purified polysaccharide from *Neisseria meningitidis* serotype W has O-acetylation levels >0.3 mMol/gm, protein impurity <5%, nucleic acid impurity <2%, and endotoxin impurity <50 EU/μg.

20. The method of claim 7, wherein the concentration of sodium hydroxide in solution is in the range of 8-15 mM.

* * * * *